United States Patent [19]

Spillert et al.

[11] Patent Number: 4,632,919

[45] Date of Patent: Dec. 30, 1986

[54] PROCESS FOR PROLONGING RECALCIFICATION, PROTHROMBIN AND THROMBIN TIMES OF PLASMA

[75] Inventors: Charles R. Spillert, West Orange, N.J.; Corinne Devereux, Bronxville, N.Y.; Eric J. Lazaro, Jersey City, N.J.

[73] Assignee: University of Medicine & Dentistry of N.J., Newark, N.J.

[21] Appl. No.: 655,145

[22] Filed: Sep. 27, 1984

[51] Int. Cl.$^4$ ............... A61K 31/635; A61K 31/505
[52] U.S. Cl. ................................ 514/158; 514/275
[58] Field of Search ............ 424/229, 251; 514/158, 514/275

[56] References Cited

U.S. PATENT DOCUMENTS 3,985,876  10/1976  Hazlett et al. ............... 424/229

*Primary Examiner*—Jerome D. Goldberg
*Attorney, Agent, or Firm*—Weiser & Stapler

[57] ABSTRACT

There is disclosed a process for prolonging recalcification, prothrombin and thrombin times of human plasma which comprises administering to a warm-blooded animal a composition selected from the group consisting of 5-methyl-3-sulfanilamidoisoxazole, a salt of 5-methyl-3-sulfanilamidoisoxazole with a pharmaceutically acceptable base, 2,4-diamino-5-(3,4,5-trimethoxybenzyl) pyrimidine, a salt of 2,4-diamino-5-(3,4,5-trimethoxybenzyl) pyrimidine with a pharmaceutically acceptable acid and mixtures thereof.

8 Claims, No Drawings

PROCESS FOR PROLONGING RECALCIFICATION, PROTHROMBIN AND THROMBIN TIMES OF PLASMA

FIELD OF THE INVENTION

This invention relates to a process for treating human plasma, and more particularly to a process for treating a warm-blooded animal to prolong recalcification, prothrombin and thrombin times of the plasma thereof.

BACKGROUND OF THE INVENTION

In U.S. Pat. No. 2,909,522, there is disclosed 2,4-diamino-5-(3,4,5-trimethoxybenzyl)pyrimidine and a process for preparing same. In U.S. Pat. No. 2,888,455, there is disclosed 5-methyl-3-sulfanilamidoisoxazole and a process for preparing same. In U.S. Reissue Pat. No. 28,636 there is disclosed a therapeutically active antibacterial composition comprising 5-methyl-3-sulfanilamidoisoxazole, or a salt thereof together with a pharmaceutically acceptable base and 2,4-diamino-5-(3,4,5-trimethoxybenzyl)pyrimidine or a salt thereof with a pharmaceutically acceptable acid.

In patients receiving an anticoagulant, such as warfarin, a mixture of such aforementioned compounds are known to prolong prothrombin times.

SUMMARY OF THE INVENTION

To increase recalcification, prothrombin and thrombin times of human plasma there is administered to a warm-blooded animal a therapeutically effective amount of an anticoagulant/antithrombotic composition selected from the group consisting of 5-methyl-3-sulfanilamidoisoxazole, a salt of 5-methyl-3-sulfanilamidoisoxazole with a pharmaceutically acceptable base, 2,4-diamino-5-(3,4,5-trimethoxybenzyl)pyrimidine, a salt of 2,4-diamino-(3,4,5-trimethoxybenzyl)pyrimidine with a pharmaceutically acceptable acid and mixtures thereof.

DETAILED DESCRIPTION OF THE INVENTION

Plasma recalcification time is the time interval between the addition of calcium ions to plasma and the detection of a fibrin clot. When performed in test tubes this determination is inherently inaccurate and difficult to standardize. However, employing a Sonoclot ® coagulation analyzer, accurate and reproducible records of viscoelastic changes occuring during fibrin formation, produces an excellent method for determining anticoagulant properties of a drug.

The prothrombin time is a measure of the extrinsic pathway of coagulation. In addition to measuring various deficiencies in coagulation factors, the prothrombin time is sensitive to anticoagulants and diminished quantities of fibrinogen present in plasma.

The addition of thrombin to plasma converts the fibrinogen to fibrin and is a measure of the availability of functional fibrinogen.

In a most comprehensive embodiment, the present invention relates to a pharmaceutical composition selected from the group consisting of 5-methyl-3-sulfanilamidoisoxazole, a salt of 5-methyl-3-sulfanilamidoisoxazole with a pharmaceutically acceptable base, 2,4-diamino-5-(3,4,5-trimethoxybenzyl)pyrimidine, a salt of 2,4-diamino-5-(3,4,5-trimethoxybenzyl)pyrimidine with a pharmaceutically acceptable acid and mixtures thereof, useful in prolonging recalcification, prothrombin and and thrombin times of human plasma.

In a more particular embodiment, the present invention relates to a pharmaceutical composition, in suitable intravenous or oral dosage forms, which composition is selected from the group consisting of 5-methyl-3-sulfanilamidoisoxazole, a salt of 5-methyl-3-sulfanilamidoisoxazole with a pharmaceutically acceptable base, 2,4-diamino-5-(3,4,5-trimethoxybenzyl)pyrimidine, a salt of 2,4-diamino-5-(3,4,5-trimethoxybenzyl)pyrimidine with a pharmaceutically acceptable acid and mixtures thereof, useful in prolonging recalcification, prothrombin and thrombin times of human plasma.

The expression "salts thereof with pharmaceutically acceptable bases" utilized throughout the present specification to denote salts of 5-methyl-3-sulfanilamidoisoxazole, preferably includes those formed utilizing an alkali metal base, such as sodium hydroxide, potassium hydroxide, etc.

The expression "salts thereof with pharmaceutically acceptable acids" utilized throughout the present specification to denote salts of 2,4-diamino-5-(3,4,5-trimethoxybenzyl)pyrimidine, preferably includes those formed utilizing mineral acids, such as hydrochloric acid, sulfuric acid, etc.; and organic acids, such as acetic acid, citric acid, lactic acid, maleic acid, salicylic acid, etc.

It is also within the scope of this invention to administer each active component individually. Thus, it is possible to formulate each of the components into separate dosage forms in accordance with procedures hereinbefore and hereinafter described for the combination.

The compositions of this invention are prepared simply by admixing 5-methyl-3-sulfanilamidoisoxazole or a salt thereof with a pharmaceutically acceptable base and 2,4-diamino-5-(3,4,5-trimethoxybenzyl)pyrimidine or a salt thereof with pharmaceutically acceptable acid.

In addition to the therapeutically active ingredients mentioned heretofore, the compositions of this invention can contain, as optional ingredients, any of the various adjuvants which are used ordinarily in the production of pharmaceutical preparations. Thus, for example, in formulating the present compositions into the desired intravenous form, one may use, as optional ingredients, anticoagulants such as warfarin, heparin, antiplatelets such as aspirin, prostaglandins ($E_1$ and $I_2$), and fibrinolytic agents such as streptokinase. It should be fully understood, however, that the optional ingredients herein named are given by way of example only and that the invention is not restricted to the use hereof. On the contrary, other such adjuvants, the identity and use of which are well known in the art, can be, and are, employed in carrying out this invention.

The ratios in which the therapeutically active components are utilized in the compositions of this invention can be varied within wide limits. For example, the compositions can contain from about 1 to about 30 parts of 5-methyl-3-sulfanilamidoisoxazole or an equivalent amount of salt thereof to about 30 to about 1 part of 2,4-diamino-5-(3,4,5-trimethoxybenzyl)pyrimidine or an equivalent amount of salt thereof, preferably from about 5 to about 15 parts of 5-methyl-3-sulfanilamidoisoxazole or an equivalent amount of a salt thereof to one part of 2,4-diamino-5-(3,4,5-trimethoxybenzyl)pyrimidine or an equivalent amount of salt thereof.

The composition of the present invention can be administered in unit dosage forms which contain 500 mg. of 5-methyl-3-sulfanilamidoisoxazole or an equivalent amount of a salt thereof and from about 25 mg. to about 100 mg. of 2,4-diamino-5-(3,4,5-trimethoxybenzyl)pyrimidine or an equivalent amount of a salt thereof. However, it is also within the scope of this invention to utilize a unit dosage form which will contain from about 250 mg. to about 800 mg. of 5-methyl-3-sulfanilamidoisoxazole or an equivalent amount of a salt thereof and from about 12.5 mg. to about 160 mg. of 2,4-diamino-5-(3,4,5-trimethoxybenzyl)pyrimidine or an equivalent amount of a salt thereof. The frequency with which any such unit dosage form will be administered to a warm-blooded animal will vary, depending upon the quantity of medicament present therein and the needs and requirements of the warm-blooded animal. Under ordinary circumstances, however, about a total of 60 mg./kg. of 5-methyl-3-sulfanilamidoisoxazole and about a total of 8 mg./kg. of 2,4-diamino-5-(3,4,5-trimethoxybenzyl)pyrimidine, in combination, can be administered daily in several doses.

As hereinabove discussed, detailed description is made with reference to unit dosages whether in intravenous or oral form, the frequency and dosage levels are best related with regard to antithrombotic/anticoagulant effectiveness in terms of component levels in the plasma of the warm-blooded animals being treated of the composition selected from the group consisting of 5-methyl-3-sulfanilamidoisoxazole, a salt of 5-methyl-3-sulfanilamidoisoxazole with a pharmaceutically acceptable base, 2,4-diamino-5-(3,4,5-trimethoxybenzyl)pyrimidine, a salt of 2,4-diamino-5-(3,4,5-trimethoxybenzyl)pyrimidine with a pharmaceutically acceptable acid and mixtures thereof. Generally, it is preferably desired to maintain in the plasma of the warm-blooded animal a component level of the 5-methyl-3-sulfanilamidoisoxazole or an equivalent amount of the salt thereof of from about 80 to 160, preferably about 110 $\mu$g./cc. and/or a component level of the 2,4-diamino-5-(3,4,5-trimethoxybenzyl)pyrimidine or an equivalent amount of the salt thereof of from about 5 to 15, preferably 10 $\mu$g./cc.

This invention relates to the invention described in copending applications Ser. Nos. 655,079; 655,227; 655,080; and 655,144 filed on even date herewith, the teachings of which are incorporated) by reference herein.

The foregoing, notwithstanding, it should be fully understood that the dosages set forth herein are examplary only and they do not, to any extent, limit the scope or practice of the present invention. As indicated hereinbefore, the combination of this invention has unexpectedly been found to be particularly useful in prolonging the recalcification, prothrombin and thrombin times of human plasma.

The invention will be understood better by reference to the following examples which are given for illustration purposes and are not meant to limit the invention.

EXAMPLE 1

Recalcification Time of Human Citrated Platelet-Poor Plasma

Ten microliters of 0.5M CaCl$_2$ is added to 0.4 cc. of plasma containing varying amounts of the drugs to be tested or an equal volume of the drug vehicle only. The Sonoclot ® analysis is performed according to the manufacturers's directions and the time necessary for sample viscosity to be equivalent to a one inch rise from baseline viscosity values was taken as the endpoint.

The plasma samples were prepared by adding various volumes of I.V. infusion containing trimethoprim (16 mg./cc.) and sulfamethoxazole (80 mg./cc.) compounded with 40% propylene glycol, 10% ethyl alcohol and 0.3% diethanolamine; 1% benzyl alcohol and 0.1% sodium metabisulfite as preservatives and pH adjusted to approximately 10 with sodium hydroxide to plasma.

The drug vehicle was comprised of 40% propylene glycol, 10% ethyl alcohol and 1% benzyl alcohol plus water and NaOH to bring pH to approximately 10. For each determination of the effects of the I.V. infusion (Injectable Composition I.C. 80 mg./cc. sulfamethoxazole/16 mg./cc. trimethoprim, thimethoprim (16 mg./cc.) or sulfamethoxazole (80 mg./cc.)) on the recalcification time of each plasma, an equal volume of the drug's vehicle was also evaluated as set forth in Tables I, II and III, below. In addition, the effects of the drug vehicle was compared to that of saline and no significant differences were observed below 70 $\mu$l cc. (PPP).

TABLE I

| Volume of IV(IC) or Vehicle (V) Added to 1 cc. PPP | Mean Recalcification Time (min.) ± SD | Significance |
|---|---|---|
| 0.5 $\mu$l V | 8.69 ± 2.22 | p < .05 |
| 0.5 $\mu$l IC | 11.10 ± 3.71 | |
| 1.0 $\mu$l V | 10.10 ± 2.62 | NS |
| 1.0 $\mu$l IC | 11.23 ± 4.78 | |
| 2.0 $\mu$l V | 10.13 ± 2.66 | p < .05 |
| 2.0 $\mu$l IC | 12.73 ± 4.01 | |
| 3.0 $\mu$l V | 10.81 ± 4.45 | NS |
| 3.0 $\mu$l IC | 11.53 ± 3.91 | |
| 4.0 $\mu$l V | 9.61 ± 2.37 | p < .05 |
| 4.0 $\mu$l IC | 11.97 ± 3.75 | |
| 5.0 $\mu$l V | 9.64 ± 2.64 | NS |
| 5.0 $\mu$l IC | 10.56 ± 2.85 | |
| 10.0 $\mu$l V | 9.31 ± 1.55 | p < .02 |
| 10.0 $\mu$l IC | 12.35 ± 3.48 | |
| 15.0 $\mu$l V | 9.81 ± 2.18 | p < .01 |
| 15.0 $\mu$l IC | 16.72 ± 5.95 | |
| 30.0 $\mu$l V | 7.87 ± 1.32 | p < .001 |
| 30.0 $\mu$l IC | 19.50 ± 7.00 | |

TABLE II

| Volume of Sulfamethoxazole (S, 80 mg./cc.) or Vehicle (V) Added to 1 cc. PPP | Mean Recalcification Time (min.) ± SD | Significance |
|---|---|---|
| 1 $\mu$l V | 6.03 ± 2.18 | NS |
| 1 $\mu$l S | 7.98 ± 3.59 | |
| 5 $\mu$l V | 5.72 ± 1.68 | NS |
| 5 $\mu$l S | 6.90 ± 2.87 | |
| 10 $\mu$l V | 6.22 ± 2.18 | p < .05 |
| 10 $\mu$l S | 6.97 ± 2.65 | |
| 30 $\mu$l V | 5.10 ± 1.21 | p < .05 |
| 30 $\mu$l S | 6.63 ± 2.05 | |
| 50 $\mu$l V | 6.08 ± 1.34 | p < .05 |
| 50 $\mu$l S | 7.62 ± 2.14 | |

TABLE III

| Volume of Trimethoprim (T, 16 mg./cc.) or Vehicle (V) Added to 1 cc. PPP | Mean Recalcification Time (min.) ± SD | Significance |
|---|---|---|
| 4 $\mu$l V | 7.16 ± 1.35 | NS |
| 4 $\mu$l T | 6.52 ± 0.64 | |
| 10 $\mu$l V | 7.00 ± 0.85 | NS |
| 10 $\mu$l T | 7.68 ± 1.91 | |
| 40 $\mu$l V | 8.38 ± 1.34 | NS |
| 40 $\mu$l T | 9.22 ± 1.91 | |
| 70 $\mu$l V | 6.66 ± 0.93 | p < .01 |

TABLE III-continued

| Volume of Trimethoprim (T, 16 mg./cc.) or Vehicle (V) Added to 1 cc. PPP | Mean Recalcification Time (min.) ± SD | Significance |
|---|---|---|
| 70 μl T | 10.58 ± 1.94 | |

EXAMPLE 2

Prothrombin Time

To 1 cc. of human plasma was added various volumes of I.V. infusion or vehicle. After adding the test material, mixing and incubating for three minutes 0.1 cc. to sample was added to a fibrometer cell and 0.2 cc. of 1:1 thromboplastin:0.035M CaCl$_2$ was added to start the reaction. The fibrometer detects fibrin strand formation and records the time for this end-point to develop. A minimum of three determinations were run for each sample and the results averaged as set forth in Table IV below.

TABLE IV

| Volume of IV(IC) or Vehicle (V) Added to 1 cc. PPP | Mean Prothrombin Times (sec.) ± SD | Significance |
|---|---|---|
| 5 μl V | 39.88 ± 7.70 | NS |
| 5 μl IC | 41.35 ± 9.60 | |
| 10 μl V | 41.03 ± 7.46 | NS |
| 10 μl IC | 43.05 ± 8.88 | |
| 15 μl V | 37.78 ± 6.19 | p < .05 |
| 15 μl IC | 44.13 ± 8.64 | |
| 30 μl V | 38.48 ± 6.46 | p < .02 |
| 30 μl IC | 50.48 ± 10.76 | |
| 40 μl V | 34.55 ± 13.21 | p < .05 |
| 40 μl IC | 61.33 ± 28.50 | |
| 50 μl V | 37.13 ± 5.96 | p < .01 |
| 50 μl IC | 59.10 ± 10.42 | |

EXAMPLE 3

Thrombin Time

Samples were prepared in the identical manner as for the prothrombin time determinations of Example 2. To 0.1 cc. of plasma sample in the fibrometer was added 0.2 cc. of 5 units/cc. thrombin to initiate the conversion of fibrinogen to fibrin. All samples were done in triplicate and the results averaged as set forth in Table V below.

TABLE V

| Volume of IV(IC) or Vehicle (V) Added to 1 cc. PPP | Mean Thrombin Time (sec.) ± SD | Significance |
|---|---|---|
| 15 μl V | 22.13 ± 2.35 | p < .05 |
| 15 μl IC | 24.37 ± 2.69 | |
| 30 μl V | 22.13 ± 2.35 | p < .001 |
| 30 μl IC | 27.30 ± 3.06 | |
| 50 μl V | 22.13 ± 2.35 | p < .001 |
| 50 μl IC | 31.43 ± 4.39 | |

When calcium is added to plasma, most of the time necessary to form a clot is consumed in the production of prothrombin activator (plasma thromboplastin stage 1). Only seconds are required to convert prothrombin to thrombin (stage 2) and fibrinogen to fibrin (stage 3). Therefore, since an I.V. infusion composition, or its components individually prolonged the recalcification times, the anticoagulant properties may in part be attributed to the slowing of the enzymatic conversions necessary to produce thromboplastin. Furthermore, the I.V. infusion composition prolongs prothrombin and thrombin times, delaying stages 2 and 3. Thus, the I. V. infusion composition is believed in vitro affects all stages of plasma clotting and passes clinical uses as an anticoagulant or antithrombotic agent.

Although the I.V. composition significantly inhibited clotting at volumes of 0.5, 2.0 and 4.0 μl per cc. PPP, it consistently produced prolonged recalcification times at 10 μl or greater. Sulfamethoxazole prolonged clotting at 10 μl whereas trimethoprim required more than 40 μl to be effective.

EXAMPLE 4

The effect of the Injectable Composition (IC) on thromboplastin (TBN) activated clotting. TBN is the most potent activator of the clotting system. Whether IC can influence the activated clotting induced by TBN was studied. To 1 cc. of human platelet poor plasma (n=8) was added 10 μl saline or varying volumes of IC. After 10 minutes of incubation 10 μl of a 1% TBN solution was added and Sonoclot ® analysis performed. The results are set forth in Table VI below:

TABLE VI

| Volume of IV(IC) or Vehicle (V) Added to 1 cc. PPP | Mean Recalcification Time (min.) ± SD for TBN Activated Plasmas | Significance |
|---|---|---|
| 10 μl V | 3.83 ± .46 | — |
| 2 μl IC | 4.53 ± .45 | p < .01 |
| 5 μl IC | 4.85 ± .65 | p < .001 |
| 10 μl IC | 5.14 ± 2.49 | p < .01 |

The IC at the concentrations utilized reduce the increased thrombatic tendency (prolong recalcification times) induced by TBN.

Numerous modifications and variations of the present invention are possible in light of the above teachings and, therefore, within the scope of the appended claims, the invention may be practiced otherwise than as particularly described.

What is claimed is:

1. A process for treating a warm-blooded animal to prolong at least one of recalcification, prothrombin or thrombin time of plasma which comprises administering to a warm-blood animal in need of such treatment (a) at least one member selected from the group consisting of 5-methyl-3-sulfanil-amidoisoxazole and a salt of 5-methyl-3-sulfanilamidoisoxazole with a pharmaceutically acceptable base and (b) at least one member selected from the group consisting of 2,4,-diamino-5-(3,4,5-trimethoxybenzyl)pyrimidine and a salt of 2,4-diamino-5-(3,4,5-trimethoxybenzyl)pyrimidine with a pharmaceutically acceptable acid, said components (a) and (b) being administered in an amount effective to prolong at least one of recalcification, prothrombin or thrombin time.

2. The process as defined in claim 1 wherein said therapeutically effective amount of the composition comprises from about 250 mg. to about 800 mg. of 5-methyl-3-sulfanilamidoisoxazole or an alkali metal salt thereof with a pharmaceutically acceptable base and from about 12.5 mg. to 160 mg. of 2,4-diamino-5-(3,4,5-trimethoxybenzyl)pyrimidine or a salt thereof with a pharmaceutically acceptable acid.

3. The process as defined in claim 1 wherein a component level in the plasma of the warm-blooded animal of said 5-methyl-3-sulfanilamidoisoxazole or an alkali metal salt thereof with a pharmaceutically acceptable base is maintained at from about 80 to 160 μg./cc.

4. The process as defined in claim 3 wherein said component level is preferably about 110 μg./cc.

5. The process as defined in claim 1 wherein a component level in the plasma of the warm-blooded animal of said 2,4-diamino-5-(3,4,5-trimethoxybenzyl)pyrimidine or a salt thereof with a pharmaceutically acceptable acid is maintained at from about 5 to 15 μg./cc.

6. The process as defined in claim 5 wherein said component level is preferably about 10 μg./cc.

7. The process of claim 1 wherein components (a) and (b) are administered separately.

8. The process of claim 1 wherein components (a) and (b) are administered together.

* * * * *